United States Patent [19]

Shiraishi et al.

[11] Patent Number: 4,699,680
[45] Date of Patent: Oct. 13, 1987

[54] PROCESS AND APPARATUS FOR MANUFACTURING ELEMENT FOR ELECTROPHORESIS

[75] Inventors: Hisashi Shiraishi; Mineo Suyefuji; Masashi Kato, all of Minami-ashigara, Japan

[73] Assignee: Director of the Finance Division Minister's Secretariat Science and Technology Agency, Tokyo, Japan

[21] Appl. No.: 716,952

[22] Filed: Mar. 28, 1985

[30] Foreign Application Priority Data

Mar. 29, 1984 [JP] Japan .................. 59-61667

[51] Int. Cl.[4] .................. B29C 39/00; B32B 31/18
[52] U.S. Cl. .................. 156/242; 156/246; 156/267; 156/500; 156/501; 156/510; 264/212; 204/180.1; 204/180.2; 204/180.4; 204/181.1
[58] Field of Search .................. 156/242, 246, 267, 268, 156/290, 500, 501, 510; 264/212; 204/180.1, 180.2, 180.4, 181.1

[56] References Cited

U.S. PATENT DOCUMENTS

| | | | |
|---|---|---|---|
| 2,129,607 | 9/1938 | Schott | 156/246 |
| 3,120,037 | 2/1964 | Schribner | 264/212 |
| 3,392,077 | 7/1968 | Brieske et al. | 156/513 |
| 3,429,957 | 2/1969 | Merten | 264/212 |
| 3,860,473 | 1/1975 | Wesen | 156/267 |
| 4,295,907 | 10/1981 | Cordts et al. | 156/246 |

Primary Examiner—Caleb Weston
Attorney, Agent, or Firm—Jules E. Goldberg

[57] ABSTRACT

A process of manufacturing an element for electrophotresis which comprises steps of: sticking a spacer continuously to both side portions of a support web which is rolled back continuously from the rolled condition; casting on said support a solution for forming a medium membrane for electrophoresis; subjecting the support to hardening treatment to form a medium membrane; cutting off a portion of the medium membrane and support web; and sticking a cover sheet onto the medium membrane. An apparatus advantageously employable for performing the above process is disclosed.

7 Claims, 3 Drawing Figures

PROCESS AND APPARATUS FOR MANUFACTURING ELEMENT FOR ELECTROPHORESIS

BACKGROUND OF THE INVENTION

1. Field of the Invention

This invention relates to a process for manufacturing flat-type element for electrophoresis comprising a medium membrane placed between two sheets and an apparatus advantageously employable for performing the process. More particularly, this invention is to provide a process and an apparatus for manufacturing an element for electrophoresis which is easy to handle and advantageously employable for performing autoradiography.

2. Description of Prior Arts

A procedure of flat-type electrophoresis is performed based on the fact that substances in a conductive medium membrane migrate differently in the electric field depending upon the nature of the substance. Electrophoresis is regarded inevitable for separation and analysis of substances originating from living body such as protein and nucleic acid in biochemistry and medical science. Particularly, the flat-type electrophoresis is inevitable in the procedure for determination of base sequence of DNA which is frequently performed in genetic engineering or study of hereditary disease, because it is required to compare respective migration distances of four kinds of base-specifically cleaved DNA products or mixtures of base-specifically chain prolonged DNA products.

In the conventional process for flat-type electrophoresis, a polymer gel lacking in self-supporting nature such as agarose and polyacrylamide is used in the form of membrane (layer) which is prepared by forming a gel on a support or between two supports. However, the gel formed on a support is easily broken in the procedure of forming the gel on a support, a procedure of placing the gel in a device for electrophoresis, storage of the gel or a procedure of applying a sample on the gel. Further, the gel is sometimes damaged by inadvertently dropping something other than sample on the gel. Accordingly, much attention and skill are required to handle it. In a conventional process of vertical electrophoresis wherein a mold is made of two glass plates for forming a gel therebetween and the mold is kept vertical in the electrophoresis procedure, it is difficult to prepare a mold with uniform thickness and is also difficult to introduce a gel forming solution into a mold of narrow space before the solution becomes gel. Therefore, specific skill is also required. Particularly, in the procedure for determination of base sequence of DNA, it is desired to prepare a long gel medium so as to analyze DNA segments as many as possible. It is, however, difficult to prepare and to handle such a long gel medium. It is further disadvantageous that the glass plate is easily broken.

In the procedure of electrophoresis, the components to be analyzed in an analyte are labeled with radioisotope and separated through electrophoresis. Subsequently, the image of the separated components in the analyte is given by autoradiography. This process includes a procedure of placing the medium membrane for electrophoresis containing radioisotope on a radiographic film for recording the radiation emitted therefrom in layers and allowing to stand them (this procedure is called "exposure"). During this procedure, it is required, in the case that the flat type gel membrane is employed, to cover the radiographic film with a water impermeable thin sheet such as a plastic wrapping sheet to prevent the film from wetting. In the case that a gel is formed between two glass plates, it is required to replace one glass plate with a thin film (for keeping the radiation emitted from isotope in analyte in the gel from being absorbed and remarkably reduced which takes place when a radiation passes through a glass plate). In this procedure of removing the glass plate, it often happens that a gel is inadvertently broken, or a portion of the gel is sticked to the upper glass plate and the other portion of the gel is sticked to the lower glass plate. Therefore, skill is required to remove one glass plate without damaging the gel. Further, when the gel medium is covered with a thin sheet such as a plastic wrapping sheet, foams are sometimes introduced and left between the gel and sheet, or the sheet is apt to be wrinkled, thereby decreasing adhesiveness between the gel and the radiographic film. As a result, the obtained autoradiograph is apt to be unclear and the resolution nature decreases.

As a result of study by the present inventors for obviating the above defects, they have discovered that a flat-type element for electrophoresis provided with a medium membrane for electrophoresis between a support and a cover sheet having thickness of not more than 50 $\mu$m is easy to handle in the procedure of electrophoresis and the subsequent exposure and recording procedures without possibility of rapturing a gel medium membrane. They have already applied the above invention for patent under the Japanese Patent Application No. 58(1983)-1324.

The above-mentioned invention has an advantage that a gel medium membrane employed as a medium for electrophoresis is easy to handle without possibility of being broken. Moreover, in the case that a self-supporting porous membrane (e.g., continuous micro-porous membrane of cellulose acetate, filter paper) is employed as a medium membrane, said invention can also gives the above advantage.

SUMMARY OF THE INVENTION

An object of the present invention is to provide a process and apparatus for continuously, efficiently and precisely manufacturing the aforementioned novel element for electrophoresis.

There is provided by the present invention a process of manufacturing an element for electrophoresis comprising steps of sticking a spacer continuously to both side portions of a support web which is rolled back continuously from the rolled condition, casting on said support a solution for forming a medium membrane for electrophoresis (i.e., gel-forming solution), subjecting the support to hardening treatment (i.e., gelation) to form a medium membrane, cutting off a portion of the medium membrane and support web, and sticking a cover sheet onto the medium membrane.

The above process is advantageoulsy performed by the use of an apparatus comprising a casting device for casting a solution for forming a medium membrane for electrophoresis (i.e., gel-forming solution) on a continuously running support web, a casing for hardening treatment and a cutting device (e.g., punching device) for cutting off a portion of the gel medium membrane for electrophoresis, in which said cutting device is provided with a vacuum chamber.

DETAILED DESCRIPTION OF THE INVENTION

The present invention will be described in more detail by referring to preferred examples illustrated in the attacched drawings, but the invention is not limited to these examples.

Figure 1:
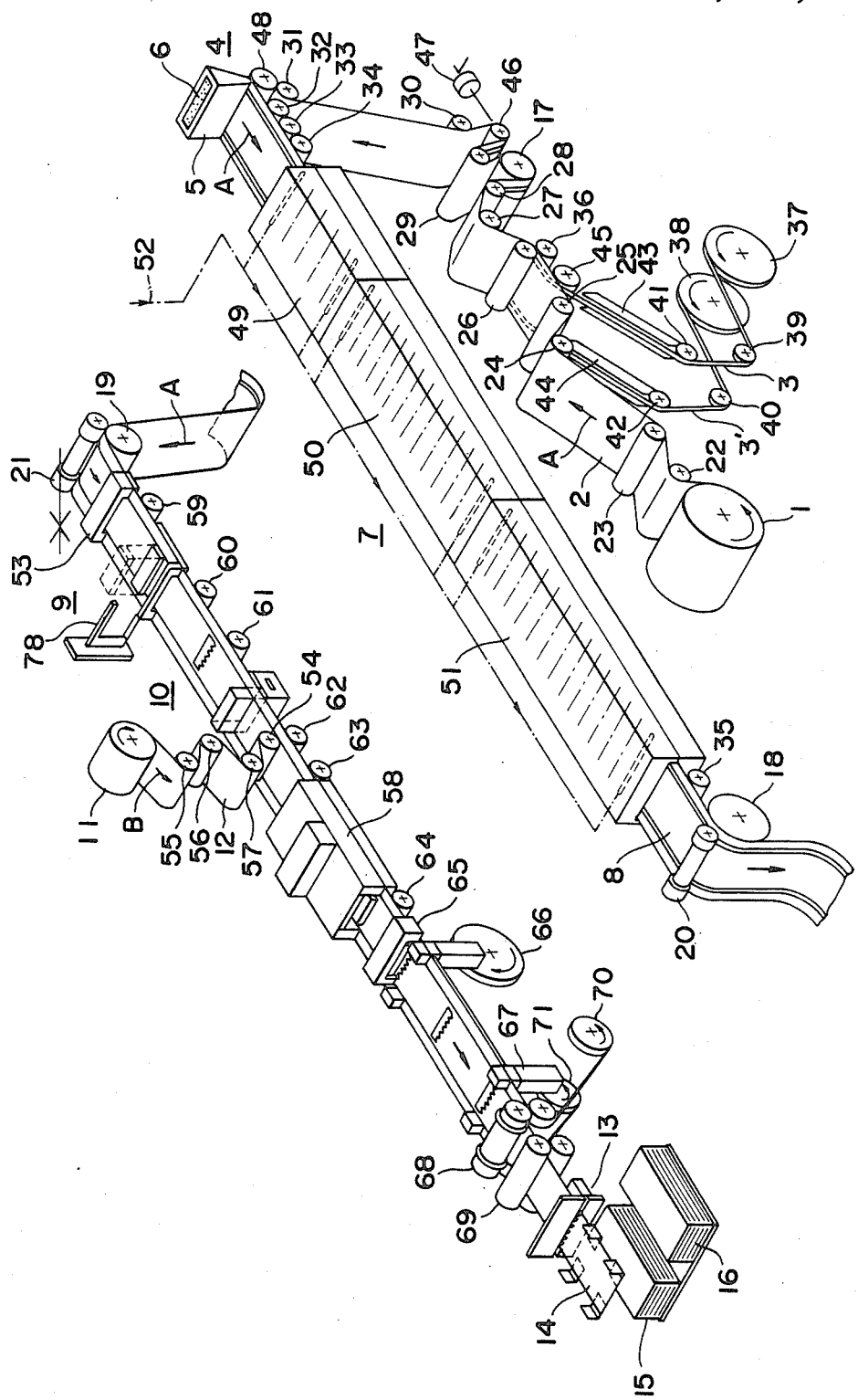
FIG. 1 is a view showing an embodiment of an apparatus according to the invention.

FIG. 1 is a schematic perspective view showing one embodiment of the process and apparatus of the invention. In FIG. 1, spacers 3 and 3' are continuously sticked to both side portions of a support web 2 rolled back continuously from rolled condition 1 in the direction shown by an arrow A and a solution for a medium for electrophoresis (gel forming solution) 6 is casted (or coated) on the support web 2 from a hopper 5 provided at a casting portion 4. The solution is subjected to hardening treatment (to make it gel through polymerization and cross-linking) when the solution passes through a casing for hardening treatment 7 to form a medium membrane 8. Subsequently, a portion of the membrane 8 and a portion of the support web 2 are cut off in combination by means of cutting devices 9 and 10 to form slots for supplying samples, and to the membrane 8 is sticked a cover sheet 12 which is intermittently rolled back from rolled condition 11 in the direction shown by an arrow B. The membrane 8 combined with the cover sheet 12 is then cut by a cutter 13 so as to give a novel element for electrophoresis 14. Numerals 15 and 16 show the elements for electrophoresis placed in layers.

In FIG. 1, suction drums 17, 18 and 19 work singly or in cooperation with pressing rollers 20 and 21 to make the support web 2 continuously run. Numerals 22, 23, 24, 25, 26, 27, 28, 29, 30, 31, 32, 33, 34, and 35 are passing rollers to help the support web 2 to run continuously. A driving roller 36 for heating adhesion sticks the spacers 3 and 3' to the both side portions of the support web 2 supplied from the rolled condition 37 and 38 through passing rollers 39, 40, 41 and 42, preheating devices 43 and 44, and a pressing roller 45. 46 is a dancer roller and 47 is a balancer. 48 shows a backing roller of the casting portion. In FIG. 1, the hopper 5 is shown as a casting device for casting a gel-forming solution. However, various kinds of systems such as a slide hopper and curtain flow can be also applied.

When the gel-forming solution 6 casted on the support web 2 passes through the casing for hardening 7, the solution 6 is preheated by a heater of far infrared rays in the first casing 49, by a heater of ultraviolet rays in the second casing 50, by a heater of far infrared rays in the third casing 51 so as to undergo hardening through photopolymerization to form a medium membrane 8 for electrophoresis in gel condition. The hardening treatment is generally performed in an atmosphere containing no oxygen, for example, in an atmosphere of nitrogen gas supplied through a tube 52.

53 is a clump device. When the support 2 which continuously runs carrying the medium membrane 8 under the gel condition arrives at the position of the clump device, then the support runs intermittently, and a portion of the medium membrane 8 and a portion of the support web are cut off by the cutting devices 9 and 10 respectively to form slots for supplying samples. The cutting devices will be described hereinafter. A driving pressing roller 54 rolls back intermittently the cover sheet 12 which is rolled in a roll 11 via passing rollers 55, 56 and 57, and sticks the sheet to the support web 2 through spacers 3, 3' and the medium membrane 8. 58 designates a casing for heat-sealing, and 59, 60, 61, 62, 63, and 64 are passing rollers for conveying the web. 65 is a clump device, and 66 and 67 are intermittent driving devices. 68 is an side-cutting device. The cut side portion is rolled up by rollers 70 and 71 to dump or to collect for certain utilization.

Figure 2:
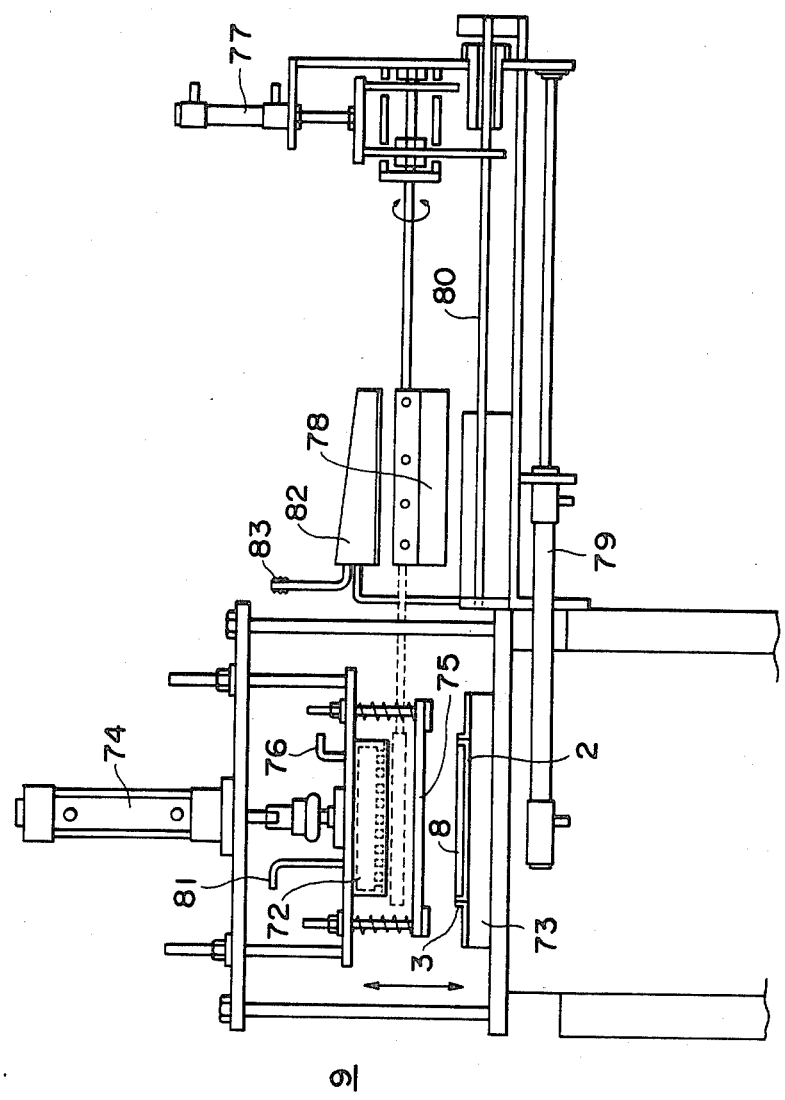
FIG. 2 is a front view showing the structure of the cutting device for the gel medium membrane for electrophoresis.

In FIG. 2, the cutting device 9 for cutting unnecessary portions out of the gel medium membrane which is one of characteristic features of the apparatus according to the invention is provided with a vacuum chamber 72. The lower portion of the vacuum chamber 72 is provided with edges arranged in the form of a comb. When the support 2 carrying the gel medium membrane 8 stops running on a supporting stand 73, an air cylinder 74 works to cause a support pressing plate 75 to clamp the support 2. Then, the vacuum chamber 72 having edges arranged in the form of a comb at the lower portion thereof comes down so as to cut off a portion of the gel medium membrane 8 to form slots for supplying samples arranged like a comb. The vacuum chamber 72 turns under the condition of reduced pressure so as to adsorb the removed portions of the gel medium membrane and ascends. Then, an air cylinder 77 works to keep a receiving plate 78 horizontal. An air cylinder 79 works to cause the receiving plate 78 to move along a rail 80 to the vacuum chamber 72. When the receiving plate 78 arrives below the chamber 72, pressurized air is sent to the vacuum chamber 72 through a pressure tube 81 so that the collected portions (e. g., in the form of chips) of gel medium membrane are dropped on the receiving plate 78. The air cylinder 79 continues to work to cause the receiving plate 78 to come back along the rail 80. Subsequently, the air cylinder 77 operates to cause the receiving plate 78 to decline. At the same time, an air knife 82 blows out the pressured air sent from the tube 83 so as to throw down the collected portions of gel medium membrane in a wast box (not shown).

Figure 3:
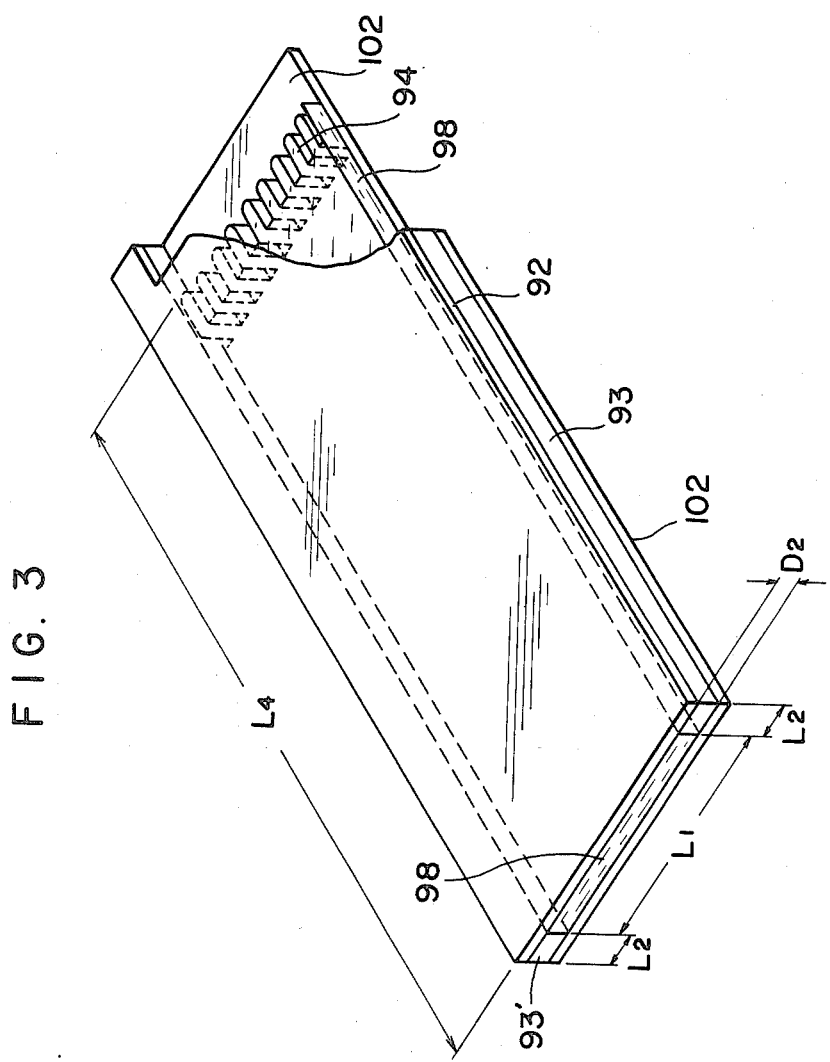
FIG. 3 is a perspective view of the structure of the element for electrophoresis manufactured according the invention.

FIG. 3 shows one example of the element of electrophoresis manufactured by the process and apparatus of the invention. Four sides of the medium membrane 98 for electrophoresis having a cut portion, that is, slots 94 for supplying samples formed by cutting off are surrounded by a support 92, spacers 93 and 93' and a cover sheet 102. A cut portion 94 arranged in the form of a comb serves as slots for introducing samples in performing vertical electrophoresis.

In the invention, various kinds of materials can be employed as cover sheets 12 and 102, and supports 2 and 92 as far as it is a non-conductive and substantially water-impermeable sheet having a smooth surface. The following substances are preferably employed: polyesters such as polyethylene terephthalate, polycarbonate of bisphenol A, vinyl polymers such as poly(methyl methacrylate), polyethylene, polystyrene and poly(vinyl chloride), polyamide such as nylon, and copolymers thereof such as a copolymer of vinylidene chloride and vinyl chloride. Materials of the cover sheet 12 and 102 and supports 2 and 92 may be the same or different.

There is no specific limitation on the medium membranes 8 and 98 for electrophoresis as far as the electrophoresis can be performed therein. Representative examples include acrylamide gel, agarose gel, starch gel, agar gel, porous membrane of cellulose acetate and filter paper. Thickness of the medium membrane ($D^2$) is determined depending on the purpose of electrophoresis. The thickness is usually within the range of 50 μm to approx. 10 mm, and preferably approx. 200 μm to approx. 5 mm for gel medium membrane, and approx. 70 μm. to approx. 1 mm for a porous membrane and filter paper. As shown in FIG. 3, the size of the medium membrane ($L^1 \times L^4$) can be determined depending on the perpose. The gel medium membrane for determination of base sequence of DNA preferably has $L^1$ of 20 cm to 40 cm and $L^4$ of 30 cm to 60 cm.

Thickness of the spacer cannot be larger than the thickness ($D^2$) of medium membrane 108. The width $L^2$ of the spacer preferably is within the range of 5 mm to 20 mm.

Since the element for electrophoresis as shown in the above examples is always provided with a cover sheet, there is little possibility to destroy the gel even even when the surface of the gel is brought into contact with a foreign substance, or the gel portion is grasped by hand. Therefore, the element for electrophoresis is easy to handle. Further, when a sample is dropped on a portion other than the opening for supplying sample, the dropped sample is easily wiped off.

Moreover, the element for electrophoresis of the invention can be subjected to autoradiography using a radiographic film after electrophoresis without involving the complicated procedure to remove the cover sheet. This brings about decrease of possibility of failure in autoradiography. The exposure procedure in autoradiography usually requires long period of time. In the case that the exposure procedure is performed in failure, the successive exposure procedure requires much longer period owing to resulting decrease of radioactivity of radioisotope. Thus, the loss in period is extremely serious.

For the above reasons, simplification of exposure procedure of autoradiography can contribute to curtail the period for experiment. Since the elements having the gel medium membrane of the invention are in the form of sheet, they can be stored in a heap. Therefore, the storage thereof does not require large space.

The present invention comprising steps of continuously sticking spacers, continuously casting the solution for the medium for electrophoresis, subjecting the solution to hardening treatment, cutting off a portion of the medium membrane for electrophoresis to form slots for supplying samples can provide a novel element for electrophoresis continuously and efficiently with high accuracy. Further, the apparatus of the invention is provided with a vacuum chamber at a cutting device. By the provision of this vacuum chamber, the cut portions of medium membrane can be discharged without fail.

We claim:

1. A process for manufacturing an element for electrophoresis comprising the steps of sticking a spacer continuously to both side portions of a support web which is rolled back continuously from the rolled condition, casting on said support a solution for forming a gel medium membrane for electrophoresis, subjecting the support on which the solution is cast to a treatment to make the solution into a gel medium membrane, cutting off a portion of the gel medium membrane and support web, and sticking a cover sheet onto the gel medium membrane.

2. The process of manufacturing an element for electrophoresis as claimed in claim 1, wherein said treatment is performed in an atmosphere of nitrogen.

3. The process of manufacturing an element for electrophoresis as claimed in claim 1, wherein said solution for forming the gel medium membrane is an an acrylamide gel-forming solution.

4. The process of manufacturing an element for electrophoresis as claimed in claim 1, wherein said cover sheet has a thickness of not greater than 50 μm.

5. An apparatus for manufacturing an element for electrophoresis which comprises a means for sticking a spacer continuously to both side portions of a continuously running support web, a casting device for casting a solution for forming a gel medium membrane for electrophoresis on the continuously running support web, a casing for treating the solution to make it into a gel medium membrane, a cutting device for cutting off a portion of the gel medium membrane, said cutting device being provided with a vacuum chamber, and means for applying a cover sheet onto the gel medium membrane.

6. The apparatus of manufacturing an element for electrophoresis as claimed in claim 5, wherein the casting device comprises a hopper.

7. The apparatus of manufacturing an element for electrophoresis as claimed in claim 5, wherein the cutting device is provided with a means for removing the cut-off portion of the gel medium membrane.

* * * * *